United States Patent [19]
Applegate, Jr.

[11] 3,970,081
[45] July 20, 1976

[54] TENNIS ELBOW BRACE

[75] Inventor: Leslie T. Applegate, Jr., Cincinnati, Ohio

[73] Assignee: Surgical Appliance Industries, Inc., Cincinnati, Ohio

[22] Filed: Jan. 28, 1974

[21] Appl. No.: 437,207

[52] U.S. Cl............................... 128/95; 128/165; 273/29 R; 2/16
[51] Int. Cl.² ......................................... A61F 5/24
[58] Field of Search ................. 128/95, 96, 99, 100, 128/101, 106, 80 C, 78, 80 R, 165, 327, 80; 273/291, 189 R, 189 A

[56] References Cited
UNITED STATES PATENTS

| | | | |
|---|---|---|---|
| 763,683 | 6/1904 | Magoris | 128/96 |
| 1,388,772 | 8/1921 | Sheehan | 128/95 |
| 1,473,041 | 11/1923 | Henderson | 128/327 |
| 1,599,762 | 9/1926 | Guthrie et al | 128/96 |
| 1,612,121 | 12/1926 | Hittenberger | 128/96 |
| 1,637,706 | 8/1927 | Pfaltzgraff | 128/96 |
| 2,641,761 | 6/1953 | Schultz | 128/165 X |
| 3,096,760 | 7/1963 | Nelkin | 128/78 |
| 3,318,305 | 5/1967 | Schultz | 128/80 R |
| 3,351,053 | 11/1967 | Stuttle | 128/78 |
| 3,586,001 | 6/1971 | Sanderson | 128/327 |
| 3,786,804 | 1/1974 | Lewis | 128/DIG. 15 |
| 3,789,842 | 2/1974 | Froimson | 128/165 |

Primary Examiner—John D. Yasko
Attorney, Agent, or Firm—Wood, Herron & Evans

[57] ABSTRACT

A support to be worn on the arm near the elbow joint for reducing pain in the elbow joint associated with the condition of tennis elbow. The support includes a tubular sleeve of one-way stretch fabric. An inelastic strap is stitched to the sleeve and encircles the arm. The strap passes through a metal loop and carries Velcro members for adjustably tensioning the strap and securing its end in place. A reversible pressure pad with one flat side and one dimpled side is located in a pocket in the sleeve disposed radially inwardly of the loop.

8 Claims, 5 Drawing Figures

TENNIS ELBOW BRACE

BACKGROUND OF THE INVENTION

This invention relates to braces or supports and is particularly directed to a support for alleviating the pain associated with a condition known as "tennis elbow". Tennis elbow is a painful condition which seems to be caused by inflammation of the ligaments that join the two bones of the forearm—the radius and the ulna—to the two spurs, or epicondylitis, on the end of the humerus, or upper arm bone.

Tennis elbow is suffered primarily by tennis players, but also afflicts athletes who engage in other sports, such as platform tennis, javelin throwing, baseball and even golf. Unfortunately, not too much is known with certainty either regarding the cause or cure of this condition. As one physician stated at a recent conference on tennis elbow:

"We do not know too much about tennis elbow. It is a sore spot in or around the joint of the radius and humerus that we believe is caused by excessive strain."

In the past, various approaches have been taken to alleviate the pain associated with this condition. These have included cortisone shots, surgery, wearing copper bracelets, and wearing a tight narrow band below the elbow on the theory that compression of the arm decreases the tension on the forearm muscles.

The principal object of the present invention is to provide a support, or brace, for relief of tennis elbow. This support can be worn by the athlete while participating in his chosen sport, for example, tennis, without interference with his play. The present brace has proven to be effective to alleviate the pain associated with tennis elbow and, in many cases, to completely eliminate it.

I have determined that in treating tennis elbow through use of a brace this condition differs from one athlete to another and that different athletes do not obtain relief in precisely the same way. Accordingly, another principal object of the present invention is to provide a tennis elbow brace which can be adapted to provide different types of support so that the user can empirically determine which type of support provides optimum relief in his particular case, and can adjust the brace to provide that support.

More particularly, the present invention is predicated upon the concept of providing a tennis elbow brace comprising a tubular sleeve which is preferably formed of knitted fabric which is stretchable at least in a circumferential direction. An inelastic strap is secured to the outer surface of the sleeve at a point spaced inwardly from one end thereof. This strap encircles the sleeve, passes through a metal loop member and is folded back upon itself. In the preferred embodiment, the free end of the strap and an area spaced from the end carry mating Velcro elements by means of which the strap can be adjustably tensioned and the free end of the strap secured in place.

In addition to these elements, the sleeve is provided with a pocket preferably formed on the interior of the sleeve. This pocket supports a removable pressure pad formed of rubber or the like. In accordance with the present invention, the pocket is disposed directly under the metal loop so that the loop is effective to apply firm inward pressure upon the pad, causing the pad in turn to apply pressure against the adjacent surface of the wearer's arm.

One of the advantages of the present sleeve is that it can be positioned upon the wearer's arm in several different locations so that pressure can be concentrated on that portion of the wearer's arm which affords him the greatest relief. Specifically, some wearer's obtain optimum relief by wearing the brace so that the pad is worn laterally in the region of the radial head. Other users find optimum relief when the pressure pad is worn medially, i.e., on top of the wearer's arm so that pressure is applied to the brachioradialis muscle.

One of the advantages of the present brace, combining both a sleeve and a tension strap, is that once it is positioned it can be maintained in that position without the use of excessive tension on the inelastic strap. Moreover, the sleeve provides the additional benefit of supplying warmth over the afflicted area.

It is still a further concept of the present invention to provide a pad which facilitates variation in pressure concentration applied to the wearer. More particularly, the pad includes one generally planar face and a conical dimple on the opposite face. Some users find optimum relief through the application of highly concentrated pressure. Such users wear the brace with the dimple pointed inwardly. When so worn, the brace is effective to apply a relatively high pressure to a small area corresponding to the size of the dimple. On the other hand, many users find such concentrated pressure ineffective or painful. Such users wear the brace with the dimple pointing outwardly and with the flat face of the pad disposed next to the wearer's arm. With the pad worn in this manner, a more uniform pressure is applied over a considerably larger area. For some users, this affords optimum relief for their particular condition.

While the precise mechanism of relief afforded by the present brace is not known with certainty, it is felt that when the pad is worn laterally in the region of the radial head, it serves to support the orbicular ligament and stabilize the radial head in its relationship to the capitellum and the proximal ulna. Moreover, when the device is worn either medially or laterally, in some cases the pressure may serve to prevent swelling and displacement and, therefore, subsequent pain of a synovial nature. Still further, the pressure pad when worn medially or laterally may change the direction of pull on the common extensor or common flexor origins just enough to prevent irritation of the underlying synovial structures and thereby prevent subsequent pain.

These and other objects and advantages of the present invention will be more readily apparent from a consideration of the following detailed description of the drawings illustrating a preferred embodiment.

In the drawings:

FIG. 2 is a perspective view of a preferred form of pressure pad.

FIG. 3 is a partial cross-sectional view of the support taken along section lines 3—3 of FIG. 1.

Figure 1:
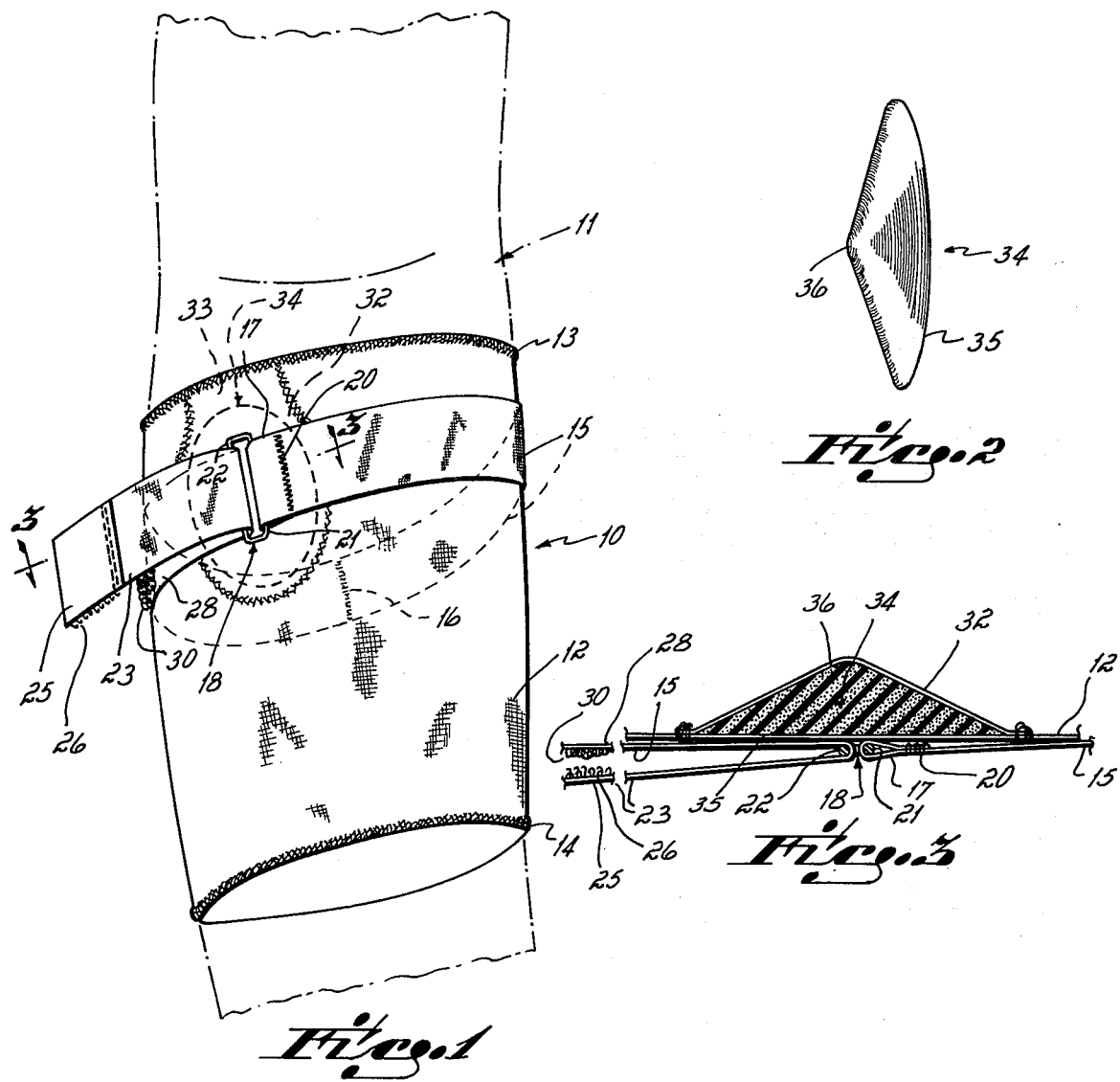
FIG. 1 shows a support of the present invention positioned on the wearer's forearm.

FIG. 1 shows a preferred form of brace 10 constructed in accordance with the present invention as positioned on the wearer's forearm just below the elbow region indicated generally at 11. The elbow brace 10 comprises a tubular sleeve 12 preferably formed of one-way stretch fabric, the fabric stretching in a circumferential direction. It is contemplated, however, that the sleeve could be formed of two-way stretch material if desired.

In the preferred embodiment, the sleeve 12 is approximately 6 inches long and tapers slightly from a large upper end 13 to a smaller lower end 14. It will, of course, be appreciated that the sleeve can be made shorter or larger if desired. In this manner, the sleeve conforms substantially to the shape of a wearer's forearm. The upper end of the sleeve carries a strap 15. Strap 15 is preferably formed of a non-stretch fabric and, in the preferred embodiment, is approximately 1½ inches wide. The strap is stitched to the outside of the sleeve along a line transverse to the length of the strap as at 16.

As shown in FIGS. 1 and 3, one end 17 of the strap passes through a metal loop member 18 and is turned back on itself and stitched to an adjacent portion of the strap as at 20 to hold the strap and loop in assembled relationship. Loop 18 is preferably formed of metal and is configurated to form an elongated narrow opening defined in part by two spaced opposed sides 21 and 22 of a length longer than the width of strap 15.

The total length of the strap 15 is appreciably in excess of the girth of the wearer's arm. Consequently, the free end 23 of the strap is sufficiently long so that it can be passed through loop 18 and folded back upon itself. The extreme free end of the strap carries one of two cooperating pieces of Velcro tape. In the preferred embodiment, tape section 25 is stitched to the inner surface of the strap and carries a plurality of hooks 26. The cooperating section 28 of Velcro tape is stitched to an opposed portion of the strap 15 and includes a plurality of loops 30. The construction of this type of Velcro fastening means is well known in the art and it is not considered necessary to go into additional detail at this point.

It is further contemplated that those skilled in the art will recognize that other forms of securement may be utilized in lieu of the Velcro tape shown. In any event, it will be appreciated that the lengths of Velcro tape are sufficiently long so that strap 15 can be secured after it has been pulled to varying degrees of tautness; and can accommodate arms of different sizes.

The inner surfaces of sleeve 12 is provided with an elongated pocket 32, the main portion of which underlies the strap 15. Pocket 32 is formed by a layer of fabric and is provided with a relatively narrow mouth 33 which can be stretched to permit the insertion and removal of a pressure pad 34.

As shown in FIGS. 2 and 3, pressure pad 34 is round in outline and includes a substantially flat surface 35 on one side and a dimpled, or conical, surface 36 on the opposite side. When pad 36 is fully inserted within the pocket 32, it lies directly under metal loop 18 as shown in FIGS. 1 and 3. Thus, when strap 15 is pulled taut, the strap is effective to press the pad inwardly to exert an inwardly directed pressure on a localized area of the wearer's arm. The pressure concentration applied to the pad is augmented by the fact that the metal rigid loop member 18 is pressing radially inwardly against the pad.

Figure 4:
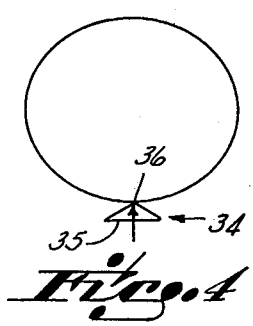
FIG. 4 is a schematic diagram showing the pressure pad with its dimpled surface facing inwardly toward the wearer's arm.
Figure 5:
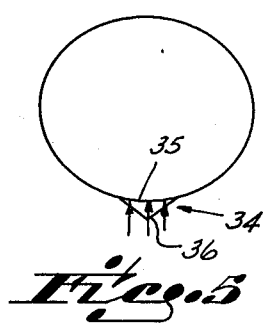
FIG. 5 is a schematic diagram showing the pressure pad with its substantially flat surface facing toward the wearer's arm.

In accordance with the present invention, the pad 34 can be reversed so as to selectively provide either a relatively high pressure directed to a relatively small area, or a more uniform pressure directed to a larger area. This is illustrated diagrammatically in FIGS. 4 and 5. As shown diagrammatically in FIG. 4 (and in detail in FIG. 3), when the pad is inserted with the dimple 36 facing inwardly, the conical point of the pad is effective to apply a concentrated pressure against a relatively small surface. The magnitude of this pressure can be adjusted by adjusting the tension of strap 15. Many wearers find that this highly concentrated pressure affords them optimum relief.

On the other hand, other wearers find this pressure objectionable or even painful. Such individuals, when wearing the brace, reverse pad 34 so that the dimple faces outwardly away from the wearer's arm. This is shown diagrammatically in FIG. 5. When the pad is worn in this fashion, the relatively flat surface 35 faces the wearer's arm and a relatively uniform pressure is applied across substantially the entire circular face of the pad.

The sleeve of the present invention can be worn in a variety of positions to provide the type of support which benefits each particular wearer. This position is determined experimentally by the wearer. The position shown in FIG. 1 is a medial position in which the pad is disposed on top of the wearer's arm above the brachioradialis muscle. It is in this position that many wearers find they obtain relief. Other users, however, find that their condition is helped most effectively by rotating the sleeve from the position shown in FIG. 1 to a lateral position in which the pad is disposed on the outside or inside of the arm in the region of the radial head. A few users may obtain benefit by raising the sleeve to a position with the pad above the elbow.

In any position, the elastic material of the sleeve and pressure pad are effective to grip the wearer's arm and function in combination with the strap to hole the brace in any desired position. It is highly significant that this retention of the brace in position can be effected with substantially less tension on the strap than is necessary when only a plain strap (without a sleeve) is utilized.

From the above disclosure of the general principles of the present invention and the preceding detailed description of a preferred embodiment, those skilled in the art will comprehend various modifications to which the invention is susceptible. Accordingly, I desire to be limited only by the scope of the following claims.

I claim:

1. Elbow brace means for alleviating the discomfort of tennis elbow comprising:
   a flexible elastic tubular sleeve for encircling the wearer's arm near the elbow, said tubular sleeve being of a size to be circumferentially stretched when disposed over the wearer's arm and having two edges;
   a resilient pad of geometric configuration mounted upon said sleeve, the maximum transverse dimension of said pad being substantially less than the circumference of and the length of said sleeve;
   a strap secured to the outside surface of said sleeve, said strap completely encircling said sleeve adjacent to, but spaced inwardly from, one of said edges;

means for securing the free end of said strap in position about said sleeve, whereby said strap is in tension;

said strap overlying said pad and being centered relative thereto, said strap being effective to exert an inwardly directed pressure upon said pad;

said pad being effective to exert a concentrated pressure upon the wearer's arm extending over an area not greater than the maximum transverse dimension of said pad, and being effective, when worn below the wearer's elbow, to change the direction of pull on the common extensor or common flexor origins.

2. Elbow brace means for alleviating the discomfort of tennis elbow comprising an elastic, tubular sleeve for encircling the wearer's arm near the elbow, said tubular sleeve being of a size such that it is stretched when placed over the wearer's arm at least in a circumferential direction and including:

a pocket spaced inwardly from one end thereof, said pocket being substantially less than the circumference of and the length of said sleeve;

a resilient pressure pad mounted within said pocket;

a strap secured to the outside surface of said sleeve, said strap completely encircling said sleeve;

means for securing the free end of said strap in position about said sleeve, whereby said strap is in tension;

said strap overlying said pocket and said pad and being effective to exert an inwardly directed pressure upon said pad;

said pad being effective to exert a concentrated pressure upon the wearer's arm extending over an area not greater than the maximum transverse dimension of said pad, and being effective, when worn below the wearer's elbow, to change the direction of pull on the common extensor or common flexor origins.

3. The elbow brace of claim 2 wherein said tubular member is constructed of a one-way stretch fabric stretchable in a circumferential direction.

4. The elbow brace of claim 2 in which said pocket is formed on the inner surface of said tubular member.

5. The elbow brace of claim 2 wherein said pressure pad has one substantially flat face and a generally conical surface.

6. The elbow brace of claim 2 in which the means for securing the free end of said strap in position include a first Velcro strip carried by the free end of said strap, and a cooperating Velcro strip secured to said strap in an area spaced from said free end.

7. The elbow brace of claim 2 in which one end of said strap carries a rigid loop, and the other end of said strap passes through said loop and is turned back upon itself, said loop overlying said pocket and said pad.

8. The elbow brace of claim 7 in which said pressure pad has one substantially flat face and an opposed face with a protuberance thereon.

* * * * *